(12) United States Patent
Takasu

(10) Patent No.: US 10,444,192 B2
(45) Date of Patent: Oct. 15, 2019

(54) ENVIRONMENT MEASURING DEVICE AND ENVIRONMENT MEASURING METHOD

(71) Applicant: FUJITSU LIMITED, Kawasaki-shi, Kanagawa (JP)

(72) Inventor: Ryozo Takasu, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 512 days.

(21) Appl. No.: 14/938,132

(22) Filed: Nov. 11, 2015

(65) Prior Publication Data

US 2016/0061777 A1    Mar. 3, 2016

Related U.S. Application Data

(63) Continuation of application No. PCT/JP2013/064513, filed on May 24, 2013.

(51) Int. Cl.
*G01N 29/02* (2006.01)
*G01N 5/02* (2006.01)
(Continued)

(52) U.S. Cl.
CPC .............. *G01N 29/022* (2013.01); *G01N 5/02* (2013.01); *G01N 29/036* (2013.01); *G01N 29/30* (2013.01);
(Continued)

(58) Field of Classification Search
CPC ........... G01N 5/02; G01N 2291/02845; G01N 2291/021; G01N 2291/0256;
(Continued)

(56) References Cited

U.S. PATENT DOCUMENTS 4,808,538 A * 2/1989 Roffey ................... G01N 17/00
422/53
5,208,162 A * 5/1993 Osborne ................. G01N 17/04
324/71.2
(Continued)

FOREIGN PATENT DOCUMENTS

JP     5-508712    12/1993
JP     2001-99777   4/2001
WO    91/17423    11/1991

OTHER PUBLICATIONS

CNOA—Office Action of Chinese Patent Application No. 201380076759.1 dated Dec. 13, 2016, with English translation of the Office Action. *JP2001199777 cited in the CNOA was previously submitted in the IDS filed on Nov. 11, 2015.
(Continued)

*Primary Examiner* — Octavia Hollington
(74) *Attorney, Agent, or Firm* — Fujitsu Patent Center

(57) ABSTRACT

An environment measuring device 1 has a measuring QCM sensor 10, a reference QCM sensor 20, a measurement oscillation circuit 15, a reference oscillation circuit 25, a frequency counter 31, a humidity sensor 51, a control unit 40, and a storage unit 41. The measuring QCM sensor 10 has an oscillator and an electrode formed by a corrosive metal on the surface of the oscillator, and the reference QCM sensor 20 has an oscillator and an electrode formed by a corrosion-resistant metal on the surface of the oscillator. The storage unit 41 stores the measurement count signal, the reference count signal, and the humidity signal which are associated with a measurement time. The control unit 40 determines an amount of increase in mass due to the corrosion of the electrode of the measuring QCM sensor by using the measurement count signal and the reference count signal.

6 Claims, 16 Drawing Sheets

(51) Int. Cl.
*G01N 29/036* (2006.01)
*G01N 29/30* (2006.01)
*G01N 29/44* (2006.01)
*G01N 27/12* (2006.01)

(52) U.S. Cl.
CPC ....... *G01N 29/4427* (2013.01); *G01N 27/121* (2013.01); *G01N 2291/021* (2013.01); *G01N 2291/0256* (2013.01); *G01N 2291/0258* (2013.01); *G01N 2291/02809* (2013.01); *G01N 2291/0426* (2013.01)

(58) Field of Classification Search
CPC ... G01N 2291/0258; G01N 2291/2291; G01N 2291/02809; G01N 2291/0426; G01N 27/121; G01N 29/022; G01N 29/036; G01N 29/30; G01N 29/4427; G01N 27/29; G01N 27/022; G01N 29/447; G01N 29/02; G01H 13/00
USPC ....................... 73/24.04, 24.06, 24.01; 436/6
See application file for complete search history.

(56) References Cited

U.S. PATENT DOCUMENTS

| | | | | |
|---|---|---|---|---|
| 7,036,375 | B2* | 5/2006 | Nozaki | G01G 3/13 73/24.06 |
| 7,814,795 | B2* | 10/2010 | Lee | G01G 3/16 73/54.24 |
| 9,645,115 | B2* | 5/2017 | Tanabe | G01N 29/022 |
| 10,006,885 | B2* | 6/2018 | Ushigome | G01N 29/022 |
| 2010/0107735 | A1 | 5/2010 | Pavlovsky | |
| 2015/0082865 | A1* | 3/2015 | Ozaki | G01N 29/036 73/24.06 |

OTHER PUBLICATIONS

CNOA—Office Action of Chinese Patent Application No. 201380076759.1 dated Jul. 20, 2017, with full English translation of the Office Action. ** References discussed in the CNOA were previously submitted in the IDS filed Feb. 16, 2017 and Nov. 11, 2015.

JPOA—Japanese Office Action (Notice of Reasons for Rejection) dated Oct. 18, 2016 for Japanese Patent Application No. 2015-518028, with English translation. **JP2001-099777 cited in the above listed JPOA was previously submitted in the IDS filed on Nov. 11, 2015.

* cited by examiner

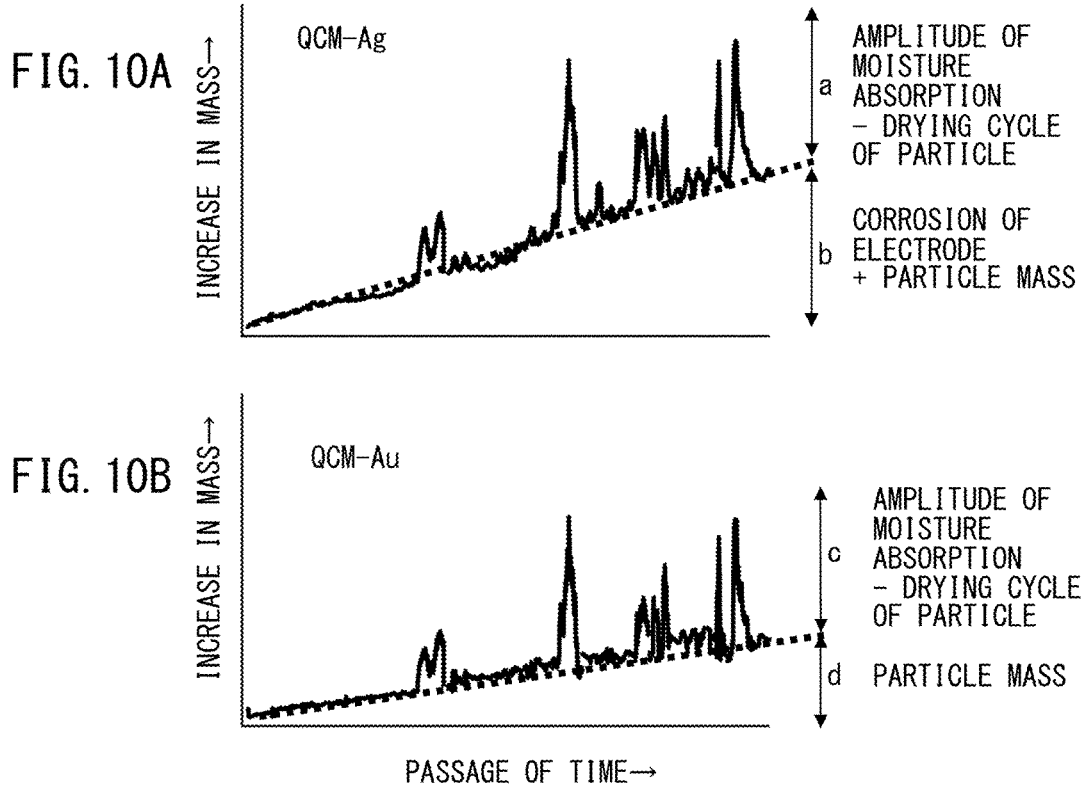

ENVIRONMENT MEASURING DEVICE AND ENVIRONMENT MEASURING METHOD

CROSS-REFERENCE TO RELATED APPLICATION

This application is a continuation application of International Patent Application No. PCT/JP2013/064513, filed on May 24, 2013, and designated the U.S., the entire contents of which are incorporated herein by reference.

FIELD

The present invention relates to an environment measuring device and an environment measuring method.

BACKGROUND

Electronic equipment, such as a server and an electronic computer, is installed inside buildings, such as factories and office buildings. A corrosive gas, such as hydrogen sulfide and sulfur dioxide, is often included in an environment in which electronic equipment is installed. The corrosive gas may deteriorate the performance of electronic equipment by corroding members, such as metal, forming the electronic equipment and further, may disable the operation of the electronic equipment. It is preferable to continuously monitor the corrosive gas in the environment in which the electronic equipment is installed before and after the installation of the electronic equipment in order to guarantee operation of the electronic equipment.

A QCM (Quartz Crystal Microbalance) sensor is known as a sensor for monitoring a corrosive gas. The QCM sensor is a mass sensor that has a quartz oscillator and an electrode formed on the surface of the quartz oscillator. The QCM sensor uses a phenomenon in which when the mass of the electrode increases due to corrosion, the oscillation frequency of the quartz oscillator is reduced according to the amount of corrosion. The QCM sensor is capable of detecting a change in oscillation frequency of a quartz oscillator with a very high degree of sensitivity and capable of performing measurement in a short period of time compared to that of a sensor that uses other measuring methods, such as a coupon method, and therefore the QCM sensor is adopted as an environment measuring device.

RELATED DOCUMENTS

[Patent Document 1] Japanese Laid Open Patent Document No. 2001-99777

SUMMARY

According to an aspect of the embodiments, an environment measuring device has a measuring QCM sensor, a reference QCM sensor, a measurement oscillation circuit, a reference oscillation circuit, a frequency counter, s humidity sensor, a storage unit, and a control unit. The measuring QCM sensor has an oscillator and an electrode formed by a corrosive metal on the surface of the oscillator, and the reference QCM sensor has an oscillator and an electrode formed by a corrosion-resistant metal on the surface of the oscillator. The measurement oscillation circuit transmits a measurement frequency signal having a frequency in accordance with the number of oscillations of the measuring QCM sensor as well as oscillating the measuring QCM sensor. The reference oscillation circuit transmits a reference frequency signal having a frequency in accordance with the number of oscillations of the reference QCM sensor as well as oscillating the reference QCM sensor. The frequency counter is connected to the measurement oscillation circuit and the reference oscillation circuit, counts the frequency of each of the measurement frequency signal and the reference frequency signal, and transmits a measurement count signal and a reference count signal each indicating the counted number. The humidity sensor detects humidity in the atmosphere and transmits a humidity signal indicating the detected humidity. The storage unit stores the measurement count signal, the reference count signal, and the humidity signal which are associated with a measurement time. The control unit determines an amount of increase in mass (hereinafter, mass increase amount) due to the corrosion of the electrode of the measuring QCM sensor by using the measurement count signal and the reference count signal each indicting the frequency measured at humidity equal to or less than predetermined humidity.

The object and advantages of the embodiments will be realized and attained by means of the elements and combination particularly pointed out in the claims.

It is to be understood that both the foregoing general description and the following detailed description are exemplary and explanatory and are not restrictive of the invention.

BRIEF DESCRIPTION OF THE DRAWINGS

FIG. 10A is a diagram separately illustrating the mass that increases due to the corrosion of the electrode and the adhesion of particles and the, mass fluctuation amount due to the moisture absorption—drying cycle of particles having adhered in the graph representing the change in mass with the passage of time of the measuring QCM sensor;

FIG. 10B is a diagram separately illustrating the mass that increases due to the adhesion of particles and the mass fluctuation amount due to the moisture absorption—drying cycle of particles having adhered in the graph representing the change in mass with the passage of time of the reference QCM sensor in the same environment as that in FIG. 10A

DESCRIPTION OF EMBODIMENTS

In the following, with reference to the drawings, an environment measuring device according to the present invention is explained. However, it should be noted that the technical scope of the present invention is not limited to those embodiments, however encompasses the inventions described in the claims and equivalents thereof.

First, an environment measuring device related to the present invention is explained.

Figure 1:
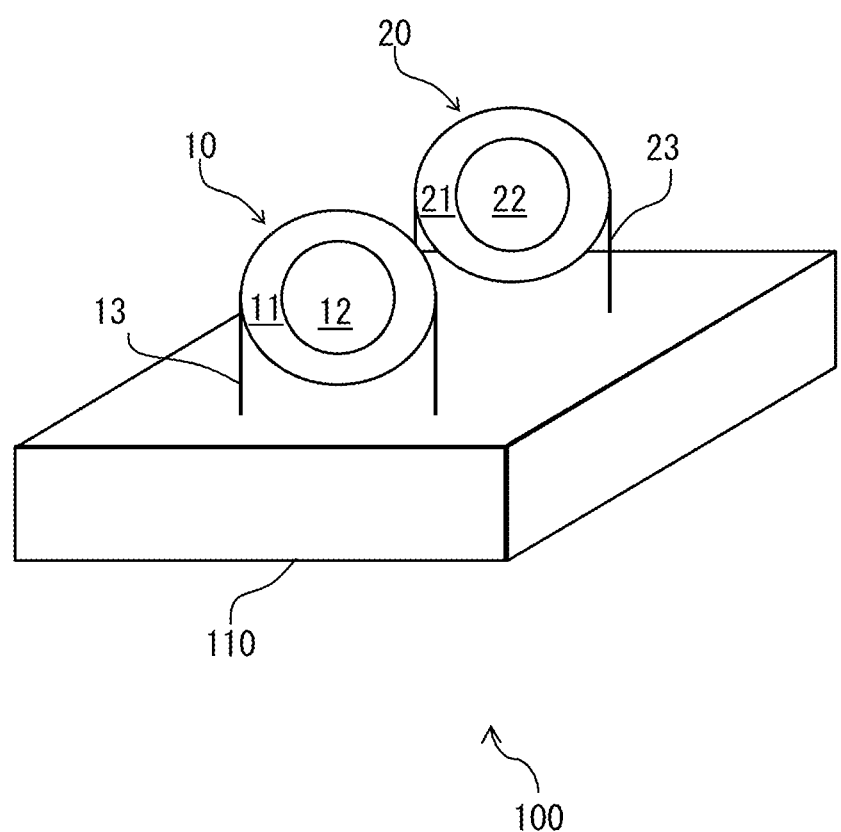
FIG. 1 is a perspective view of a related environment measuring device.
Figure 2:
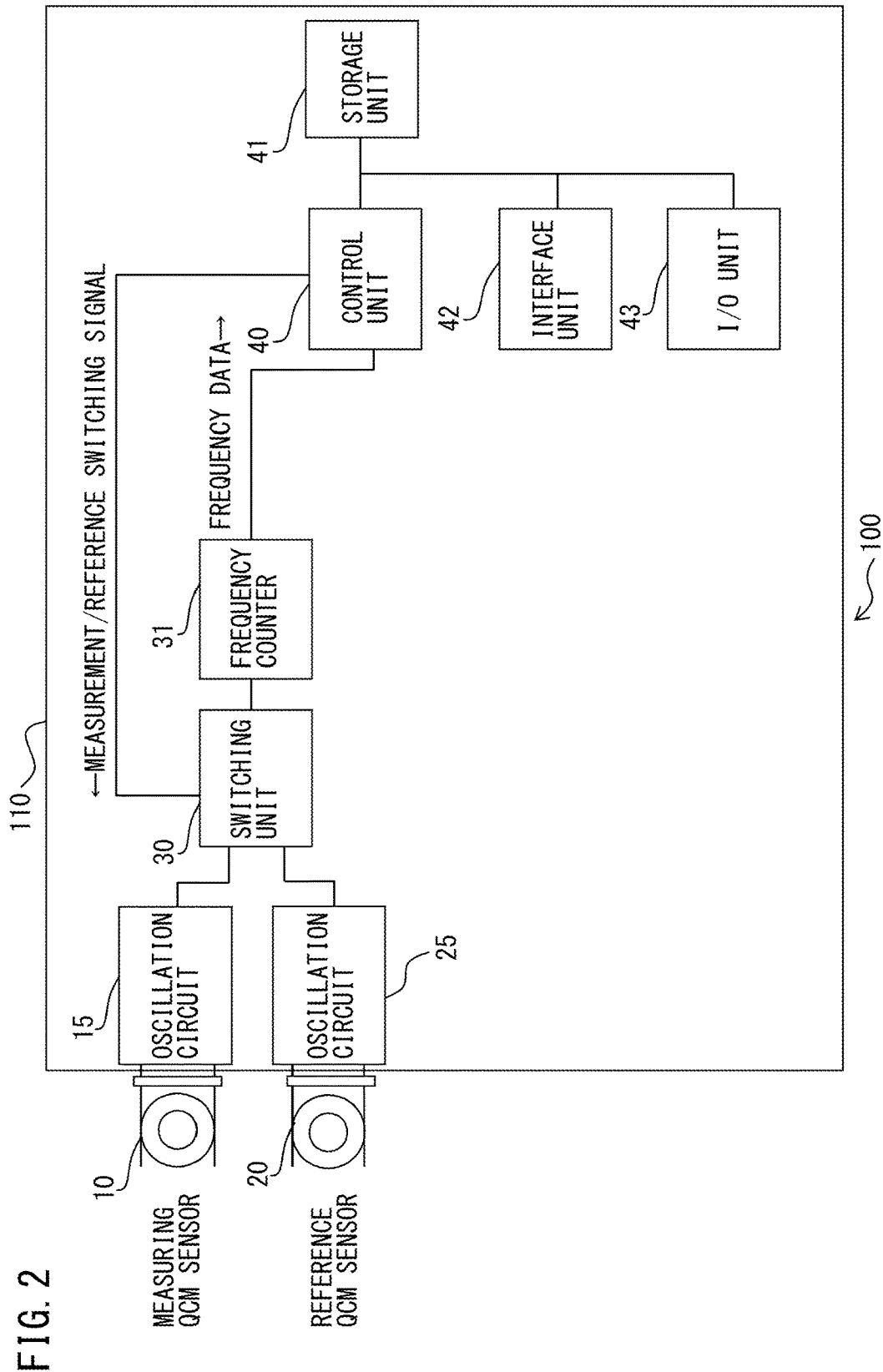
FIG. 2 is a circuit block diagram of the environment measuring device illustrated in FIG. 1.

FIG. 1 is a perspective view of a related environment measuring device and FIG. 2 is a circuit block diagram of the environment measuring device illustrated in FIG. 1.

An environment measuring device 100 has a measuring QCM sensor 10, a reference QCM sensor 20, a measurement oscillation circuit 15, a reference oscillation circuit 25, a switching circuit 30, and a frequency counter 31. The environment measuring device 100 further has a control unit 40, a storage unit 41, an interface unit 42, and an I/O unit 43.

The measuring QCM sensor 10 has a quartz oscillator 11 and a measurement electrode 12 formed on the surface of the quartz oscillator 11. The material of the measurement electrode 12 is determined by a corrosive gas that is to be measured. For example, if the corrosive gas to be measured is hydrogen sulfide, as the material of the measurement electrode 12, silver is used, and if the corrosive gas to be measured is sulfur dioxide, as the material of the measurement electrode 12, copper is used. The measuring QCM sensor 10 is connected to the measurement oscillation circuit 15 that is arranged inside a casing 110 via a metal wire 13.

The reference QCM sensor 20 has a quartz oscillator 21 and a reference electrode 22 formed on the surface of the quartz oscillator 21. A material that is unlikely to be corroded by a corrosive gas is selected as the material of the reference electrode 22. In one example, gold is used as the material of the reference electrode 22. The reference QCM sensor 20 is connected to the reference oscillation circuit 25 that is arranged inside the casing 110 via a metal wire 23.

Figure 3:
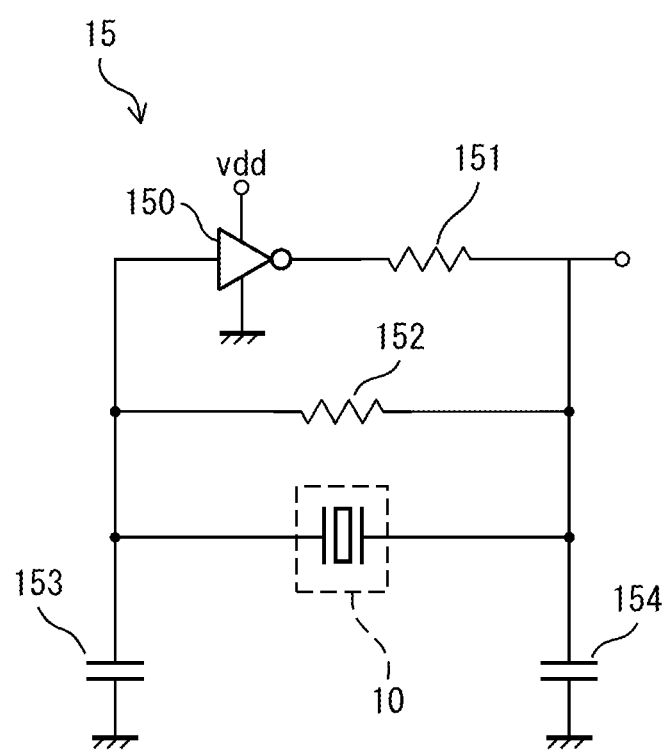
FIG. 3 is an internal circuit diagram of the measurement oscillation circuit of the environment measuring device illustrated in FIG. 1.

FIG. 3 is an internal circuit diagram of the measurement oscillation circuit 15.

The measurement oscillation circuit 15 has an inverting element 150, a first resistor 151, a second resistor 152, a first capacitor 153, and a second capacitor 154. The inverting element 150 forms a parallel resonance circuit in cooperation with the measuring QCM sensor 10. The first resistor 151 adjusts the magnitude of a crystal current that flows through the measuring QCM sensor 10. The second resistor 152 is a feedback resistor of the inverting element 150. The measurement oscillation circuit 15 outputs a frequency signal having a frequency in accordance with the number of oscillations of the measuring QCM sensor 10.

The reference oscillation circuit 25 has a configuration similar to that of the measurement oscillation circuit 15.

The switching circuit 30 selects a sensor oscillation frequency to be measured from the oscillation frequencies of the measuring QCM sensor 10 and the reference QCM sensor 20 based on a switching signal that is transmitted from the control unit 40. When the switching circuit 30 selects measuring the oscillation frequency of the measuring QCM sensor 10, the switching circuit 30 transmits the frequency of the frequency signal that is transmitted from the measurement oscillation circuit 15 to the frequency counter 31. When the switching circuit 30 selects measuring the oscillation frequency of the reference QCM sensor 20, the switching circuit 30 transmits the frequency of the frequency signal that is transmitted from the reference oscillation circuit 25 to the frequency counter 31.

The frequency counter 31 counts the frequency of the frequency signal that is transmitted from the measurement oscillation circuit 15 or the reference oscillation circuit 25 via the switching circuit 30 and transmits a counter signal indicating the counted frequency to the control unit 40.

The control unit 40 performs predetermined processing to operate the environment measuring device 100 based on a computer program stored in the storage unit 41. The storage unit 41 stores various information for operating the environment measuring device 100 as well as storing computer programs for the processing that is performed by the control unit 40.

The interface unit 42 is a touch panel, that receives commands from an operator who operates the environment measuring device 100 is input to the interface unit 42, and the interface unit 42 provides various information to the operator. The interface unit 42 displays a measurement start button and a measurement end button. When the measurement start button is pressed down, the interface unit 42 transmits a measurement start command signal, which is a signal for starting measurement, to the control unit 40. When the measurement end button is pressed down, the interface unit 42 transmits a measurement end command signal, which is a signal for ending measurement, to the control unit 40. When the interface unit 42 receives a corrosion amount signal indicating a calculated corrosion amount from the control unit 40 after the measurement ends, the interface unit 42 displays a corrosion amount corresponding to the received corrosion amount signal. The interface unit 42 displays various alerts.

The I/O unit 43 may be connected with electronic equipment, such as a personal computer and a personal digital assistant, and is an input/output terminal for exchanging various information with electronic equipment. The I/O unit 43 may receive a computer program that is executed by the control unit 40 from electronic equipment and may transmit various information stored in the storage unit 41 to electronic equipment.

Figure 4A:
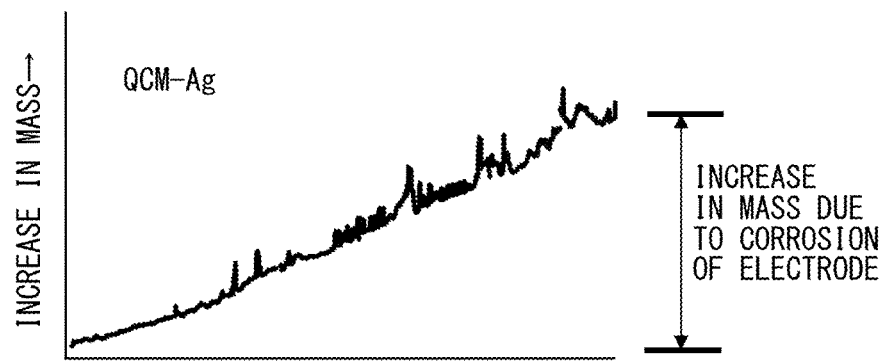
FIG. 4A is a graph representing a change in mass with the passage of time of the measuring QCM sensor in an environment in which the number of particles is small.
Figure 4B:
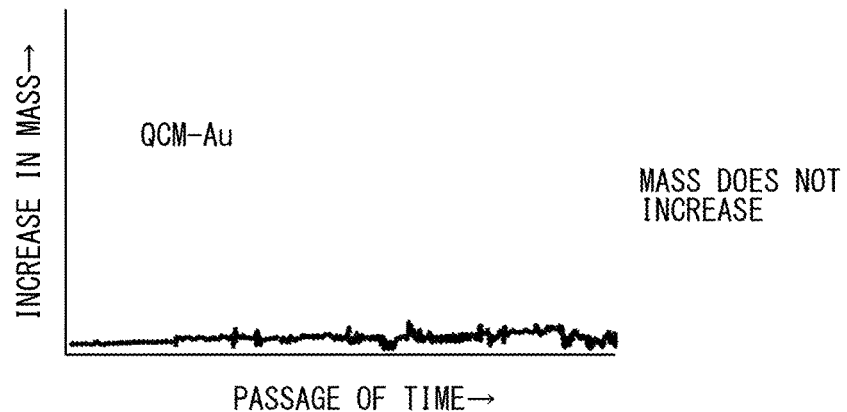
FIG. 4B is a graph representing a change in mass with the passage of time of the reference QCM sensor in the same environment as that in FIG. 4A

FIG. 4A is a graph representing a change in mass with the passage of time of the measuring QCM sensor 10 in an environment in which the number of particles is small, and FIG. 4B is a graph representing a change in mass with the passage of time of the reference QCM sensor 20 in the same environment as that in FIG. 4A.

The mass of the measuring QCM sensor 10 increases by corrosion with the passage of time. On the other hand, the mass of the reference QCM sensor 20 does not increase, since the reference electrode 22 is formed by gold having corrosion resistance, and therefore there is no increase in mass due to corrosion. The corrosion amount may be calculated based on the increase in mass of the measuring QCM sensor 10 in the environment in which the number of particles is small.

Figure 5A:
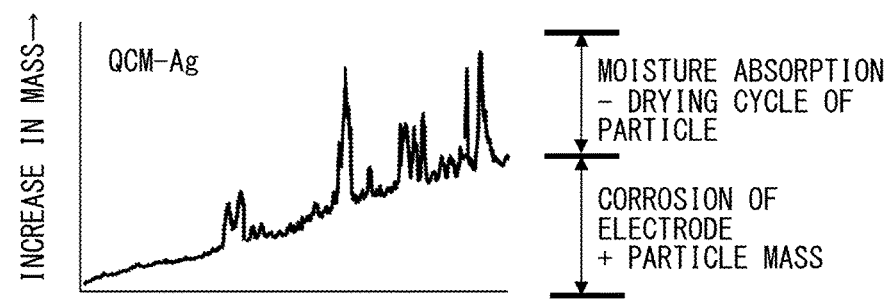
FIG. 5A is a graph representing a change in mass with the passage of time of the measuring QCM sensor in an environment in which the number of particles is larger than that in the environment in FIGS. 4A and 4B.
Figure 5B:
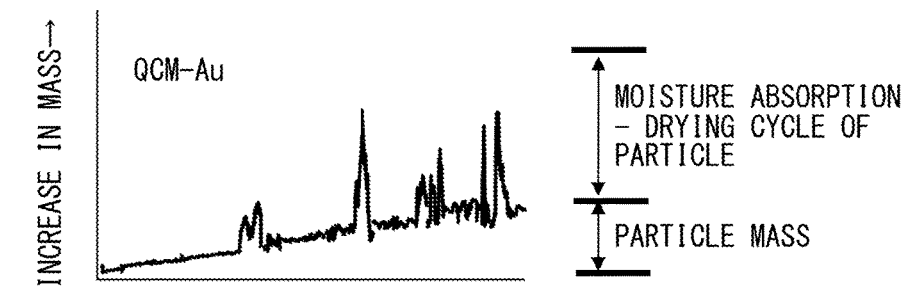
FIG. 5B is a graph representing a change in mass with the passage of time of the reference QCM sensor in the same environment as that in FIG. 5A.
Figure 5C:
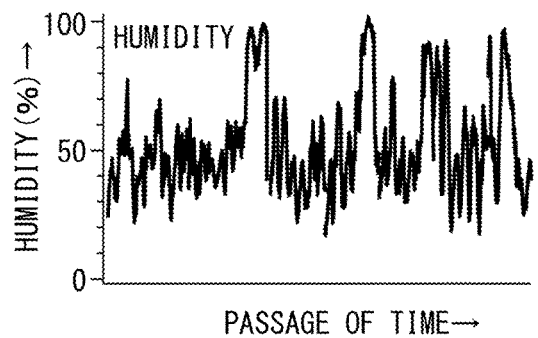
FIG. 5C is a graph representing a change in humidity with the passage of time at the time of mass measurement illustrated in the graphs in FIG. 5A and FIG. 5B.

FIG. 5A is a graph representing a change in mass with the passage of time of the measuring QCM sensor 10 in an environment in which the number of particles is larger than that in the environment in FIGS. 4A and 4B, and FIG. 5B is a graph representing a change in mass with the passage of time of the reference QCM sensor 20 in the same environment as that in FIG. 5A. FIG. 5C is a graph representing a change in humidity with the passage of time at the time of mass measurement illustrated in the graphs in FIG. 5A and FIG. 5B.

The graph illustrated in FIG. 5A represents a plurality of peak values accompanying fluctuations of mass, in addition to that the mass of the measuring QCM sensor 10 monotonically increases with the passage of time. Further, the graph illustrated in FIG. 5B represents that the mass of the reference QCM sensor 20 monotonically increases with the passage of time. Furthermore, in the graph illustrated in FIG. 5B, the mass of the reference QCM sensor 20 exhibits a plurality of peak values similar to those in the graph illustrated in FIG. 5A.

The plurality of peaks that appear in the graphs illustrated in FIGS. 5A and 5B may result from moisture absorption and drying accompanying a moisture absorption—drying cycle of the particles having adhered to the measuring QCM sensor 10 and the reference QCM sensor 20, respectively, since the peaks in the graphs illustrated in FIGS. 5A and 5B appear at the times when the humidity rises and falls.

The monotonic increase in mass with the passage of time other than the peaks that appear in the graph illustrated in FIG. 5B may result from the adhesion of particles, since the reference electrode 22 of the reference QCM sensor 20 is formed by gold having corrosion resistance, and therefore there is no increase in mass due to corrosion.

In the environment illustrated in FIGS. 5A to 5C in which the number of particles is large, it may be considered to calculate an increase in mass of the measuring QCM sensor 10 by calculating a difference between the change in mass with the passage of time of the measuring QCM sensor 10 and the change in mass with the passage of time of the reference QCM sensor 20.

Figure 6:
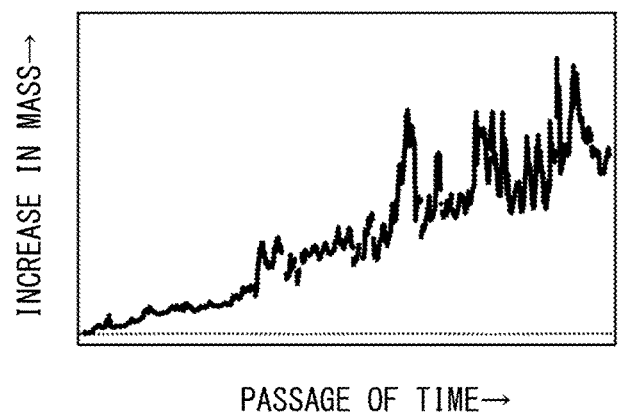
FIG. 6 is a graph representing a change with the passage of time in difference between the change in mass with the passage of time of the measuring QCM sensor illustrated in FIG. 5A and the change in mass with the passage of time of the reference QCM sensor 20 illustrated in FIG. 5B.

FIG. 6 is a graph representing a change with the passage of time in difference between the change in mass with the passage of time of the measuring QCM sensor 10 and the change in mass with the passage of time of the reference QCM sensor 20 illustrated in FIG. 5A and FIG. 5B, respectively.

Even if the difference between the change in mass with the passage of time of the measuring QCM sensor 10 illustrated in FIG. 5A and the change in mass with the passage of time of the reference QCM sensor 20 illustrated in FIG. 5B is calculated, the peaks resulting from the moisture absorption—drying cycle of particles are not removed, since the spatial distribution of particles is uneven and there is a difference between the number of particles that adhere to the measuring QCM sensor 10 and the number of particles that adhere to the reference QCM sensor 20, and therefore it is not easy to eliminate the influence of the difference between the numbers of particles that adhere.

The environment measuring device 100 may measure an increase in mass due to the corrosion of the measurement electrode 12 of the measuring QCM sensor 10 in the environment in which the number of particles is small as illustrated in FIGS. 4A and 4B. However, in the environment in which the number of particles is large as illustrated in FIGS. 5A and 5B, there occurs a phenomenon in which the mass fluctuates due to the moisture absorption—drying cycle of particles, in addition to that the mass increases, since particles adhere to the reference QCM sensor 20. In the environment in which the number of particles is large, it is not easy to determine the mass increase amount of the measuring QCM sensor 10 due to the corrosion of the measurement electrode 12 of the measuring QCM sensor 10 by eliminating the influence of the phenomenon.

Figure 7:
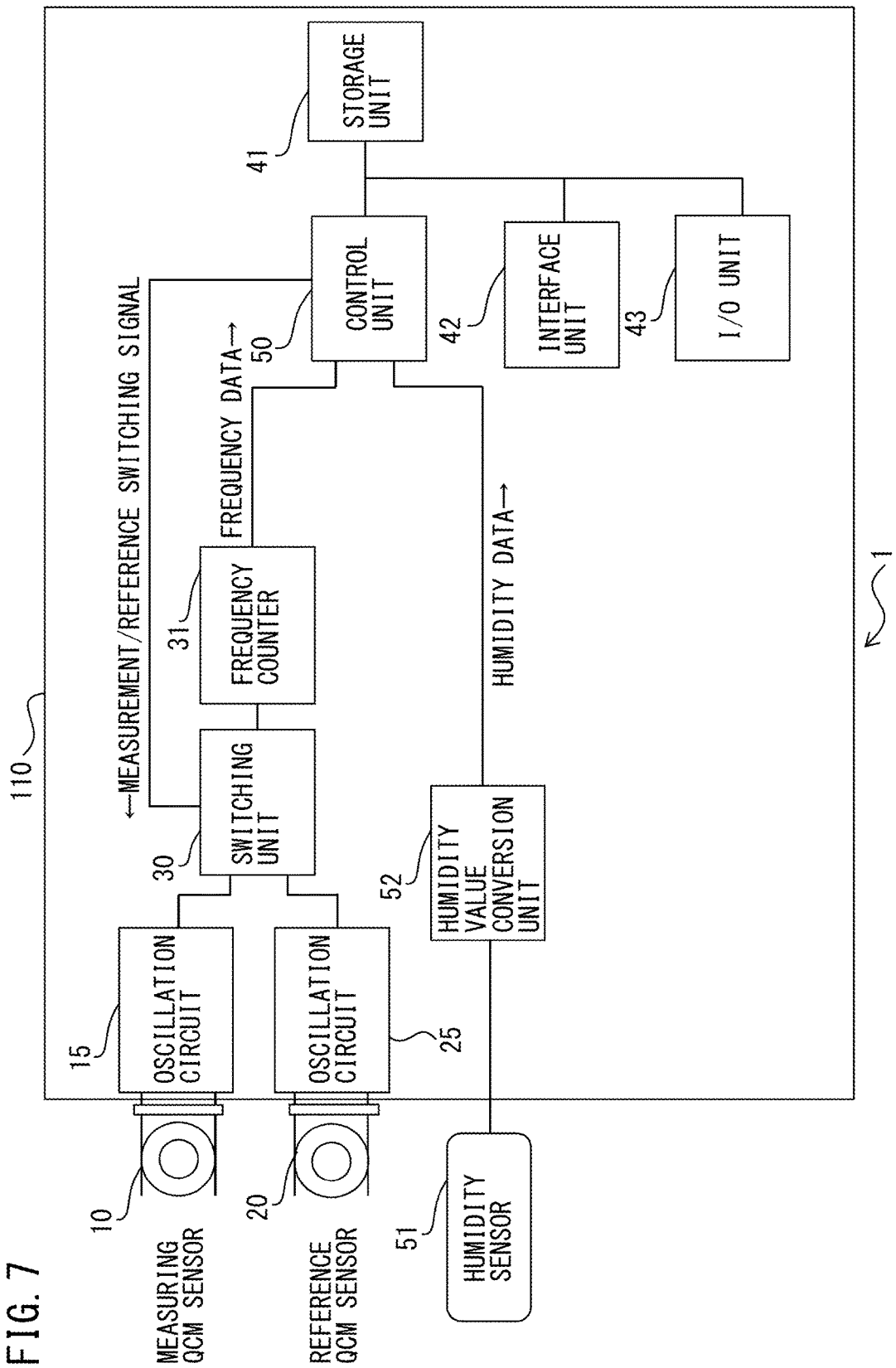
FIG. 7 is an example of a circuit block diagram of an environment measuring device

FIG. 7 is an example of a circuit block diagram of an environment measuring device.

An environment measuring device 1 differs from the environment measuring device 100 in that a control unit 50 is arranged in place of the control unit 40. Further, the environment measuring device 1 differs from the environment measuring device 100 in having a humidity sensor 51 and a humidity value conversion unit 52 configured to convert a humidity analog signal indicating the humidity detected by the humidity sensor 51 into a humidity signal, which is a digital signal.

The control unit 50 sequentially performs the following three pieces of processing. The first processing is processing to acquire a humidity signal indicating the humidity detected by the humidity sensor 51 at predetermined measurement intervals, as well as acquiring the counter signals each indicating the oscillation frequency of the measuring QCM sensor 10 and the reference QCM sensor 20. The first processing is performed in the same manner as that in the environment measuring device 100.

The second processing is processing to evaluate an increase in mass of each of the measuring QCM sensor 10 and the reference QCM sensor 20 by using the counter signal that is acquired at humidity equal to or less than a threshold value of the acquired counter signals in order to eliminate the influence of the mass fluctuations due to the moisture absorption—drying cycle of particles. The third processing is processing to evaluate the mass fluctuations due to the moisture absorption—drying cycle of particles in order to eliminate the influence of the difference in mass between the particles having adhered to the measuring QCM sensor 10 and the particles having adhered to the reference QCM sensor 20.

With reference to FIG. 8 to FIGS. 10A and 10B, the second processing that is performed by the control unit 50 in order to eliminate the influence of mass fluctuations due to the moisture absorption—drying cycle of particles is explained.

Figure 8:
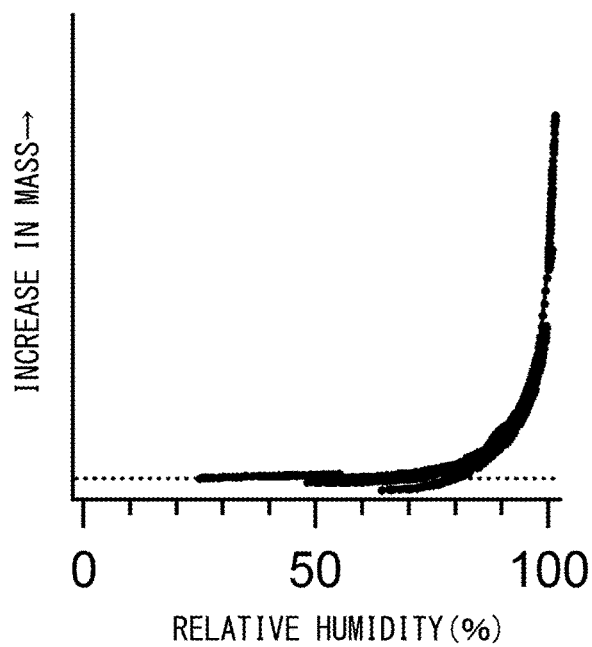
FIG. 8 is a graph representing a relationship between relative humidity and an increase in mass of the QCM sensor.

FIG. 8 is a graph representing a relationship between relative humidity and an increase in mass of the QCM sensor.

The graph illustrated in FIG. 8 represents the relationship between the mass fluctuations of the measuring QCM sensor 10 and the relative humidity in a comparatively short time, for example, about 12 hours. Since the graph illustrated in FIG. 8 is based on the mass fluctuations of the measuring QCM sensor 10 in the comparatively short time, the influence of the increase in mass of the measuring QCM sensor 10 due to corrosion may be ignored.

In the graph illustrated in FIG. 8, when the relative humidity is lower than 60%, there is no increase in mass of the measuring QCM sensor 10. On the other hand, in the graph illustrated in FIG. 8, when the relative humidity becomes higher than 60%, the mass of the measuring QCM sensor 10 increases gradually. Then, the mass of the measuring QCM sensor 10 increases sharply, when the relative humidity becomes higher than 70%.

When the relative humidity is lower than 60%, there is no increase in mass of the measuring QCM sensor 10, and therefore it may be considered that the mass fluctuations due to the moisture absorption—drying cycle of particles do not occur at the relative humidity lower than 60%. At the relative humidity lower than 60%, the mass fluctuations due to the moisture absorption—drying cycle of particles do not occur, and therefore the influence of the mass fluctuations due to the moisture absorption—drying cycle of particles is eliminated by using the counter signals acquired at the relative humidity lower than 60%.

Figure 9:
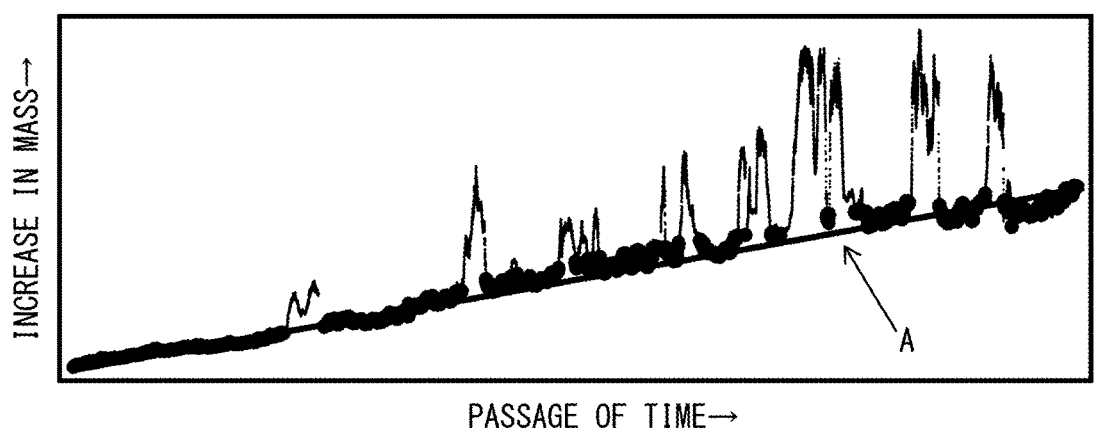
FIG. 9 is a diagram illustrating processing to extract measurement points corresponding to the counter signals acquired at the relative humidity equal to or less than 60% from the graph representing the change in mass with the passage of time of the measuring QCM sensor.

FIG. 9 is a diagram illustrating processing to extract measurement points corresponding to the counter signals acquired at the relative humidity equal to or less than 60% from the graph representing the change in mass with the passage of time of the measuring QCM sensor 10. In FIG. 9, a black dot is a measurement point corresponding to a counter signal acquired at the relative humidity lower than 60% of the counter signals of the measuring QCM sensor 10. A straight line indicated by arrow A is a straight line obtained by performing first-order approximation of the measurement points corresponding to the counter signals acquired at the relative humidity equal to or less than 60%.

The influence of the mass fluctuations due to the moisture absorption—drying cycle of particles may be eliminated from the change in mass with the passage of time of the measuring QCM sensor 10, by performing first-order approximation of and extracting the measurement points corresponding to the counter signals acquired at the relative humidity equal to or less than 60%. Similarly, the influence of the mass fluctuations due to the moisture absorption—drying cycle of particles may be eliminated from the change in mass with the passage of time of the reference QCM sensor 20 by performing first-order approximation of and extracting the measurement points corresponding to the counter signals acquired at the relative humidity equal to or less than 60%.

FIG. 10A is a diagram separately illustrating the mass that increases due to the corrosion of the electrode and the adhesion of particles and the amount of mass fluctuations (hereinafter, mass fluctuation amount) due to the moisture absorption—drying cycle of particles having adhered in the graph representing the change in mass with the passage of time of the measuring QCM sensor 10. FIG. 10B is a diagram separately illustrating the mass that increases due to the adhesion of particles and the mass fluctuation amount due to the moisture absorption—drying cycle of particles having adhered in the graph representing the change in mass with the passage of time of the reference QCM sensor 20 in the same environment as that in FIG. 10A. In FIGS. 10A and 10B, the broken line indicates a straight line obtained by performing first-order approximation of the measurement points corresponding to the counter signals acquired at the relative humidity equal to or less than 60%.

In FIG. 10A, the area under the broken line indicates the mass increase amount due to the corrosion of the electrode of the measuring QCM sensor 10 and the particles having adhered to the measuring QCM sensor 10. The area above the broken line indicates the mass fluctuation amount due to the moisture absorption—drying cycle of the particles having adhered to the measuring QCM sensor 10.

In FIG. 10B, the area under the broken line indicates the mass increase amount due to the particles having adhered to the reference QCM sensor 20 and the area above the broken line indicates the mass fluctuation amount due to the moisture absorption—drying cycle of the particles having adhered to the reference QCM sensor 20.

The mass increase amount, which is indicated by symbol b in FIG. 10A, due to the corrosion of the electrode of the measuring QCM sensor 10 and the particles having adhered to the measuring QCM sensor 10 is the mass increase amount at the measurement end time on the approximate straight line indicated by the broken line in FIG. 10A. The mass increase amount, which is indicated by symbol d in FIG. 10B, due to the particles having adhered to the reference QCM sensor 20 is the mass increase amount at the measurement end time on the approximate straight line indicated by the broken line in FIG. 10B. In the second processing, the mass increase amount of each of the measuring QCM sensor 10 and the reference QCM sensor 20 corresponding to the approximate straight line indicated by the broken line is extracted.

Figure 11A:
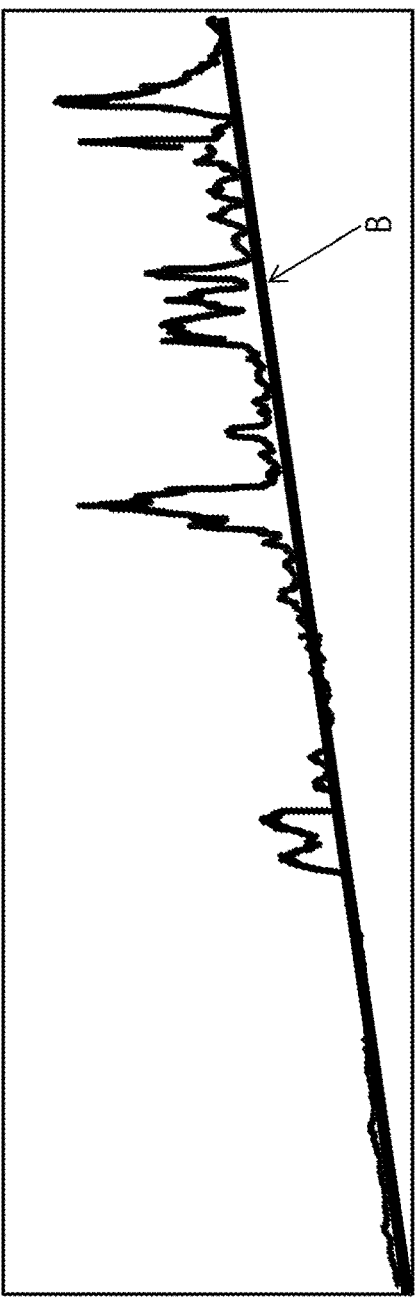
FIG. 11A is a diagram separately illustrating the mass that increases due to the corrosion of the electrode and the adhesion of particles and the mass fluctuation amount due to the moisture absorption—drying cycle of the particles having adhered to the electrode in the graph representing the change in mass with the passage of time of the measuring QCM sensor.
Figure 11B:
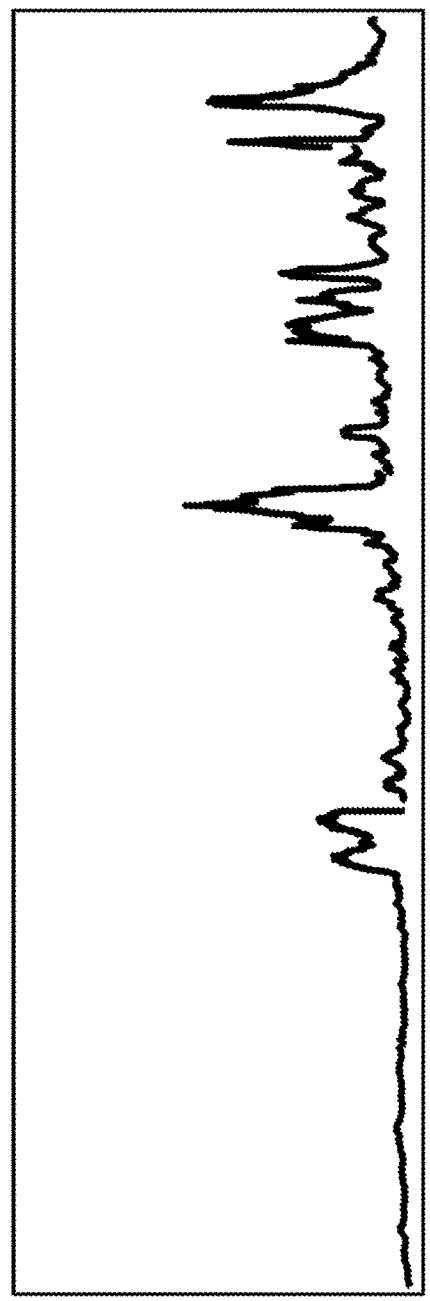
FIG. 11B is a graph obtained by extracting the mass fluctuation amount due to the moisture absorption—drying cycle of the particles having adhered to the electrode from the graph illustrated in FIG. 11A.
Figure 12:
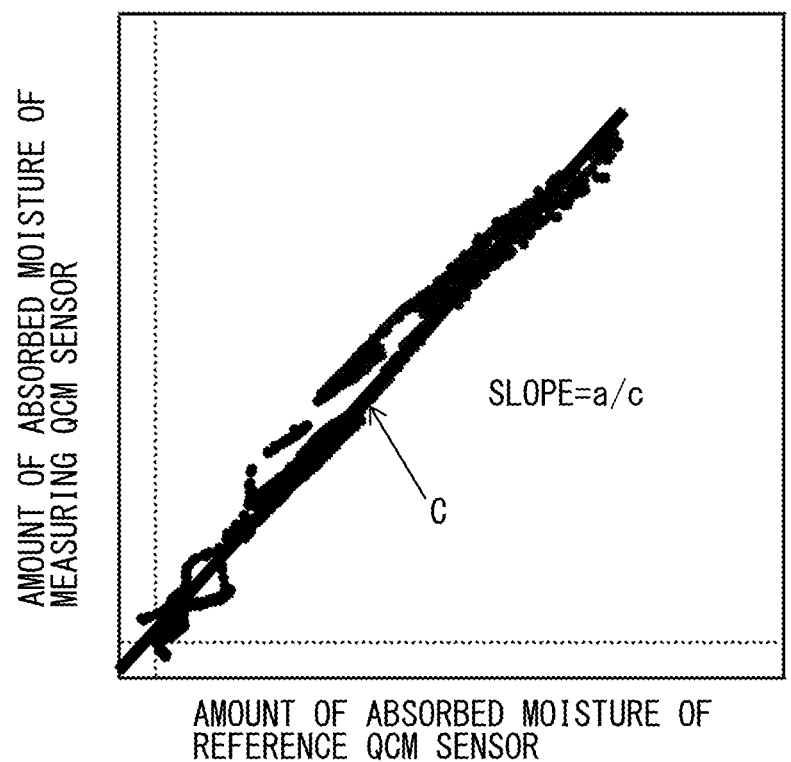
FIG. 12 is a diagram illustrating an outline of a calculation method of a correction coefficient.

With reference to FIGS. 11A and 11B and FIG. 12, the third processing that is performed by the control unit 50 in order to eliminate the influence of the difference in mass between the particles having adhered to the measuring QCM sensor 10 and the particles having adhered to the reference QCM sensor 20 is explained.

FIG. 11A is a diagram separately illustrating the mass that increases due to the corrosion of the electrode and the adhesion of particles and the mass fluctuation amount due to the moisture absorption—drying cycle of the particles having adhered to the electrode in the graph representing the change in mass with the passage of time of the measuring QCM sensor 10. FIG. 11B is a graph obtained by extracting the mass fluctuation amount due to the moisture absorption—drying cycle of the particles having adhered to the electrode from the graph illustrated in FIG. 11A.

The graph illustrated in FIG. 11B is generated by subtracting the magnitude of the measurement point corresponding to the straight line indicated by arrow B in FIG. 11A from the magnitude of each measurement point indicating the change in mass with the passage of time of the measuring QCM sensor 10.

The mass fluctuation amount corresponding to the height of the peak of each measurement point in the graph illustrated in FIG. 11B indicates the mass fluctuation amount due to the moisture absorption—drying cycle of the particles having adhered to the measuring QCM sensor 10. The mass fluctuation amount due to the moisture absorption—drying cycle of the particles having adhered to the measuring QCM sensor 10 depends on the mass of the particles having adhered to the measuring QCM sensor 10 and the humidity at the time of measurement. In particular, if the humidity is equal, it may be considered that the mass fluctuation amount due to the moisture absorption—drying cycle of the particles having adhered to the measuring QCM sensor 10 is ideally in proportion to the mass of the particles having adhered to the measuring QCM sensor 10. Although the graph illustrated in FIG. 11B represents the mass fluctuation amount due to the moisture absorption—drying cycle of the particles having adhered to the measuring QCM sensor 10, the graph representing the mass fluctuation amount due to the moisture absorption—drying cycle of the particles having adhered to the reference QCM sensor 20 may be extracted. In the graph representing the mass fluctuation amount due to the moisture absorption—drying cycle of the particles having adhered to the reference QCM sensor 20, the mass fluctuation amount corresponding to the height of the peak of each measurement point in the graph is in proportion to the mass of the particles having adhered. The mass fluctuation amount at the equal humidity corresponding to the height of the peak of the graph representing the mass fluctuation amount due to the moisture absorption—drying cycle of the particles having adhered to each of the measuring QCM sensor 10 and the reference QCM sensor 20 is in proportion to the mass of the particles having adhered to each sensor. Thus, a ratio between the mass of the particles having adhered to one of the sensors and the mass of the particles having adhered to the other is calculated by comparing the mass fluctuation amount at the equal humidity in the graph representing the mass fluctuation amount due to the moisture absorption—drying cycle of the particles having adhered to the measuring QCM sensor 10 with that in the graph representing the mass fluctuation amount due to the moisture absorption—drying cycle of the particles having adhered to the reference QCM sensor 20. The difference in mass between the particles having adhered to the measuring QCM sensor 10 and the particles having adhered to the reference QCM sensor 20 is corrected by using the calculated ratio of mass as a correction coefficient, FIG. 12 is a diagram illustrating an outline of a calculation method of a correction coefficient used to correct a difference in mass between the particles having adhered to the measuring QCM sensor 10 and the particles having adhered to the reference QCM sensor 20.

In FIG. 12, the horizontal axis represents the mass fluctuation amount due to the moisture absorption—drying cycle of the particles having adhered to the measuring QCM sensor 10 and the vertical axis represents the mass fluctuation amount due to the moisture absorption—drying cycle of the particles having adhered to the reference QCM sensor 20. Further, in FIG. 12, the black dots indicate a correlation between the mass fluctuation amount due to the moisture absorption—drying cycle of the particles having adhered to the measuring QCM sensor 10 and the mass fluctuation amount due to the moisture absorption—drying cycle of the particles having adhered to the reference QCM sensor 20 at the equal humidity.

In FIG. 12, the straight line indicated by arrow C is a straight line obtained by performing first-order approximation of the black dots. In FIG. 12, a slope a/c of the straight line indicated by arrow C is 1.2. This means that the mass of the particles having adhered to the measuring QCM sensor 10 is 1.2 times the mass of the particles having adhered to the reference QCM sensor 20.

In the third processing, a correction coefficient used to correct the difference in mass between the particles having adhered is calculated by performing the processing explained with reference to FIGS. 11A and 11B and FIG. 12. The influence of the difference in mass between the particle having adhered to the measuring QCM sensor 10 and the particles having adhered to the reference QCM sensor 20 is eliminated by using the calculated correction coefficient.

The corrosion amount of the measuring QCM sensor 10 is calculated by performing the second processing and the third processing. A corrosion amount m of the measuring QCM sensor 10 is expressed by expression (1).

$$m = b - \frac{ad}{c} \quad (1)$$

In this case, b is the mass increase amount, which is calculated by the second processing, due to the corrosion of the electrode of the measuring QCM sensor 10 and the particles having adhered to the measuring QCM sensor 10, and d is the mass increase amount, which is calculated by the second processing, due to the particles having adhered to the reference QCM sensor 20. Then, a/c is the correction coefficient that is calculated by the third processing.

Figure 13:
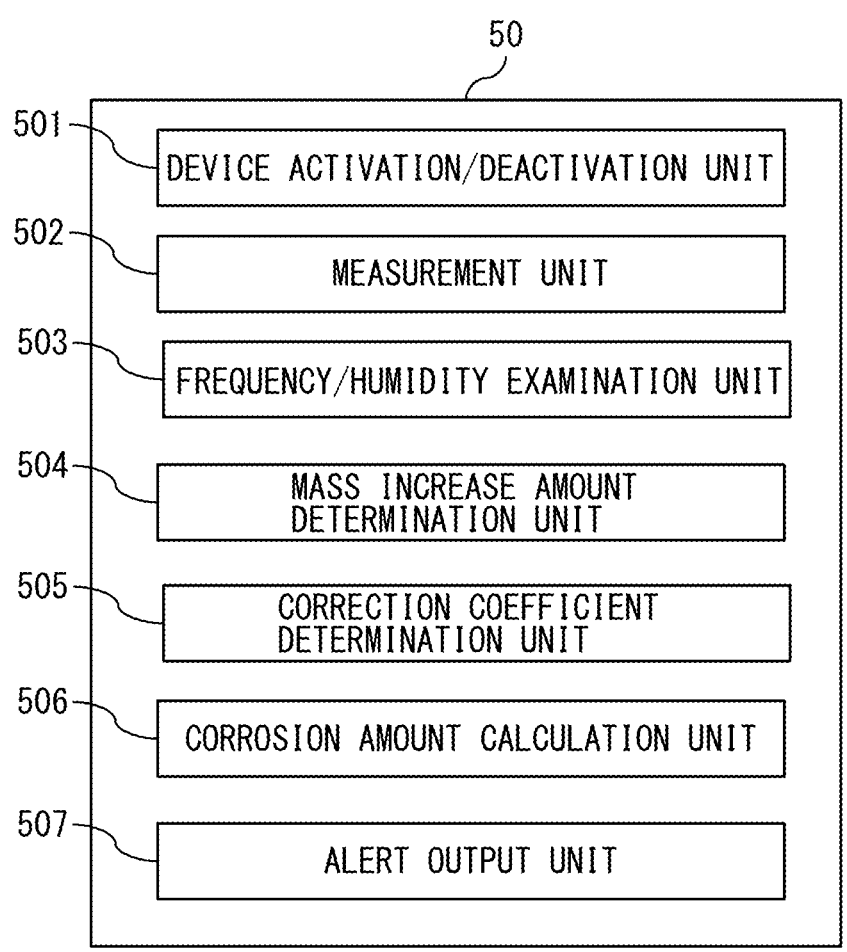
FIG. 13 is a function block diagram of the control unit.

FIG. 13 is a function block diagram of the control unit 50.

The control unit 50 has a device activation/deactivation unit 501, a measurement unit 502, a frequency/humidity examination unit 503, a mass increase amount determination unit 504, a correction coefficient determination unit 505, a corrosion amount calculation unit 506, and an alert output unit 507.

The device activation/deactivation unit 501 determines whether the measurement start command signal has been received from the interface unit 42. If the device activation/deactivation unit 501 determines that the measurement start command signal has been received from the interface unit 42, the device activation/deactivation unit 501 transmits a measurement start instruction signal to the measurement unit 502 as well as storing the current time in the storage unit 41 as a measurement start time.

The device activation/deactivation unit 501 determines whether the measurement end command signal has been received from the interface unit 42. If the device activation/deactivation unit 501 receives the measurement end command signal from the interface unit 42, the device activation/deactivation unit 501 transmits a frequency/humidity examination instruction signal to the frequency/humidity examination unit 503 as well as storing the current time in the storage unit 41 as a measurement end time.

The device activation/deactivation unit 501 determines whether an alert signal has been transmitted from the frequency/humidity examination unit 503 and the mass increase amount determination unit 504.

If the measurement unit 502 receives the measurement start instruction signal, the measurement unit 502 starts measuring the frequency of the measuring QCM sensor 10. Further, the measurement unit 502 determines whether a predetermined measurement interval period of time has elapsed by comparing the most recent measurement time of the measurement times stored in the storage unit 41 with the current time. If the measurement unit 502 determines that the predetermined measurement interval period of time has elapsed, the measurement unit 502 starts measuring the frequency of the measuring QCM sensor 10. Specifically, the measurement unit 502 transmits the switching signal to the switching circuit 30 so as to measure the oscillation frequency of the measuring QCM sensor 10. The measurement unit 502 stores the counter signal that is transmitted from the frequency counter 31 in the storage unit 41 as a measuring QCM counter signal. After storing the measuring QCM counter signal in the storage unit 41, the measurement unit 502 ends the measurement of the frequency of the measuring QCM sensor 10.

After ending the measurement of the frequency of the measuring QCM sensor 10, the measurement unit 502 starts measuring the frequency of the reference QCM sensor 20. Specifically, the measurement unit 502 transmits the switching signal to the switching circuit 30 so as to measure the oscillation frequency of the reference QCM sensor 20. The measurement unit 502 stores the counter signal that is transmitted from the frequency counter 31 in the storage unit 41 as a reference QCM counter signal. After storing the reference QCM counter signal in the storage unit 41, the measurement unit 502 ends the measurement of the frequency of the reference QCM sensor 20.

After ending the measurement of the frequency of the reference QCM sensor 20, the measurement unit 502 stores the humidity signal that is transmitted from the humidity value conversion unit 52 in the storage unit 41. After storing the humidity signal in the storage unit 41, the measurement unit 502 stores the current time as a measurement time. The measuring QCM counter signal, the reference QCM counter signal, and the humidity signal that have been stored in the storage unit 41 by the series of processing are stored in association with the current time stored as a measurement time.

The measurement unit 502 may store the frequencies and humidity of the measuring QCM sensor 10 and the reference QCM sensor 20 in time-series order. The mass increase amounts of the measuring QCM sensor 10 and the reference QCM sensor 20 are calculated from the frequencies and humidity of the measuring QCM sensor 10 and the reference QCM sensor 20 stored in time-series order.

The frequency/humidity examination unit 503 examines whether the relationship between each frequency and humidity satisfies the relationship illustrated in FIG. 8 from the relationship between the frequencies of the measuring QCM sensor 10 and the reference QCM sensor 20 and the humidity measured at the same time, which are stored in the storage unit 41. When the frequency/humidity examination unit 503 receives the frequency/humidity examination instruction signal from the device activation/deactivation unit 501, the frequency/humidity examination unit 503 starts examination processing.

The frequency/humidity examination unit 503 examines the relationship between frequency and humidity every 12 hours for each of the frequencies of the measuring QCM sensor 10 and the reference QCM sensor 20. First, when the frequency/humidity examination unit 503 examines the relationship between frequency and humidity, the frequency/humidity examination unit 503 determines whether the number of measurement points of the frequency when the humidity is 50% to 80% is larger than a predetermined threshold value. If the frequency/humidity examination unit 503 determines that the number of measurement points of the frequency when the humidity is 50% to 80% is larger than the predetermined threshold value, the frequency/humidity examination unit 503 determines whether the relationship between frequency and humidity fits to the sigmoid function. The frequency/humidity examination unit 503 determines whether a graph whose vertical axis represents the frequency and whose horizontal axis represents the humidity and which is obtained by plotting the relationship between frequency and humidity fits to the sigmoid function. If the frequency/humidity examination unit 503 determines that the relationship between frequency and humidity fits to the sigmoid function, the frequency/humidity examination unit 503 transmits a mass increase amount determination instruction signal to the mass increase amount determination unit 504 as well as storing the results of the fitting in the storage unit 41.

If the frequency/humidity examination unit 503 determines that the relationship between frequency and humidity does not fit to the sigmoid function, the frequency/humidity examination unit 503 transmits a non-fitting signal and a non-fitting time zone signal indicating the time zone during which the relationship does not fit to the sigmoid function to the alert output unit 507. After performing the determination processing on all the measuring QCM frequency signals and the reference QCM frequency signals stored in the storage unit 41, if there is no signal determined to indicate the fitting, the frequency/humidity examination unit 503 transmits a fitting fail signal to the alert output unit 507.

When the mass increase amount determination unit 504 receives the mass increase amount determination instruction signal from the frequency/humidity examination unit 503, the mass increase amount determination unit 504 starts the second processing that is performed in order to eliminate the influence of the mass fluctuations due to the moisture absorption—drying cycle of particles.

In order to perform the second processing, the mass increase amount determination unit 504 counts the number of humidity signals whose humidity corresponding to the humidity signal stored in the storage unit 41 is equal to or less than 10%. Next, the mass increase amount determination unit 504 determines whether the counted number of humidity signals is equal to or more than five. If the mass increase amount determination unit 504 determines that the counted number of humidity signals is less than five, the mass increase amount determination unit 504 counts the number of humidity signals whose humidity corresponding to the humidity signal is equal to or less than 20%, and determines whether the number of humidity signals whose humidity is equal to or less than 20% is equal to or more than five. The mass increase amount determination unit 504 repeats the same processing by increasing humidity by 10% each time until it is determined that the counted number of humidity signals is equal to or more than five. If the mass increase amount determination unit 504 determines that it is not determined that the counted number of humidity signals is equal to or more than five even by increasing the humidity up to 60%, the mass increase amount determination unit 504 transmits a calculation number shortage signal to the alert output unit 507.

If the mass increase amount determination unit 504 determines that it is determined that the number of humidity signals to be counted is equal to or more than five, the mass increase amount determination unit 504 selects the measuring QCM counter signal and the reference QCM counter signal associated with the humidity signal to be counted. Since the mass increase amount determination unit 504 selects the humidity signals in the order from the humidity signal corresponding to low humidity, the measuring QCM counter signal and the reference QCM counter signal associated with the humidity signal corresponding to low humidity are selected and the second processing is performed.

The mass increase amount determination unit 504 calculates the mass increase amount due to the corrosion of the electrode of the measuring QCM sensor 10 and the particles having adhered to the measuring QCM sensor 10 from the selected measuring QCM counter signal and the measurement time associated with the selected measuring QCM counter signal.

The mass increase amount determination unit 504 calculates the mass increase amount of the measuring QCM sensor 10 from the magnitude of the frequency corresponding to the selected measuring QCM counter signal. The mass increase amount determination unit 504 calculates an approximate straight line in which the relationship between the calculated mass increase amount of the measuring QCM sensor 10 and the measurement time is plotted. The mass increase amount determination unit 504 determines the mass increase amount due to the corrosion of the electrode of the measuring QCM sensor 10 and the particles having adhered to the measuring QCM sensor 10 from the calculated approximate straight line and the measurement end time.

The mass increase amount determination unit 504 calculates the mass increase amount due to the particles having adhered to the reference QCM sensor 20 from the selected reference QCM counter signal and the measurement time associated with the selected reference QCM counter signal.

The mass increase amount determination unit 504 calculates the mass increase amount of the reference QCM sensor 20 from the magnitude of the frequency corresponding to the selected reference QCM counter signal. The mass increase amount determination unit 504 calculates an approximate straight line in which the relationship between the calculated mass increase amount of the reference QCM sensor 20 and the measurement time is plotted. The mass increase amount determination unit 504 determines the mass increase amount due to the particles having adhered to the reference QCM sensor 20 from the calculated approximate straight line and the measurement end time.

After determining the mass increase amount due to the particles having adhered to the reference QCM sensor 20, the mass increase amount determination unit 504 transmits a correction coefficient determination instruction signal to the correction coefficient determination unit 505.

When the correction coefficient determination unit 505 receives the correction coefficient determination instruction signal from the mass increase amount determination unit 504, the correction coefficient determination unit 505 starts the third processing that is performed in order to eliminate the influence of the difference in mass between the particles having adhered to the measuring QCM sensor 10 and the particles having adhered to the reference QCM sensor 20.

The correction coefficient determination unit 505 calculates the mass fluctuation amount due to the moisture absorption—drying cycle of the particles having adhered to the measuring QCM sensor 10. In the calculation of the mass fluctuation amount, the correction coefficient determination unit 505 uses the measuring QCM counter signal stored in the storage unit 41 and the approximate straight line in which the relationship between the mass increase amount of the measuring QCM sensor 10 calculated by the mass increase amount determination unit 504 and the measurement time is plotted. The correction coefficient determination unit 505 calculates the mass increase amount of the measuring QCM sensor 10 from the magnitude of the frequency corresponding to each measuring QCM counter signal. The correction coefficient determination unit 505 subtracts the mass increase amount due to the corrosion of the electrode of the measuring QCM sensor 10 and the particles having adhered to the measuring QCM sensor 10 at the corresponding measurement time, which is calculated from the approximate straight line, from the mass increase amount of the measuring QCM sensor 10. The correction coefficient determination unit 505 calculates the mass fluctuation amount due to the moisture absorption—drying cycle of particles, which corresponds to the height of the peak of the mass fluctuations of the measuring QCM sensor 10, by the subtraction processing. The subtraction processing is performed on all the measuring QCM counter signals stored in the storage unit 41.

The correction coefficient determination unit 505 calculates the mass fluctuation amount due to the moisture absorption—drying cycle of the particles having adhered to the reference QCM sensor 20. In the calculation of the mass fluctuation amount, the correction coefficient determination unit 505 uses the reference QCM counter signal stored in the storage unit 41 and the approximate straight line in which the relationship between the mass increase amount of the reference QCM sensor 20 calculated by the mass increase amount determination unit 504 and the measurement time is plotted. The correction coefficient determination unit 505 calculates the mass increase amount of the reference QCM sensor 20 from the magnitude of the frequency corresponding to each reference QCM counter signal. The correction coefficient determination unit 505 subtracts the mass increase amount due to the particles having adhered to the reference QCM sensor 20 at the corresponding measurement time, which is calculated from the approximate straight line, from the mass increase amount of the reference QCM sensor 20. The correction coefficient determination unit 505 calculates the mass fluctuation amount due to the moisture absorption—drying cycle of particles, which corresponds to the height of the peak of the mass fluctuations of the reference QCM sensor 20, by the subtraction processing. The subtraction processing is performed on all the reference QCM counter signals stored in the storage unit 41.

The correction coefficient determination unit 505 calculates the slope of the first-order approximate straight line, which is obtained by plotting the calculated mass fluctuation amounts due to the moisture absorption—drying cycle of the particles having adhered to the measuring QCM sensor 10 and the reference QCM sensor 20 in association with humidity, as a correction coefficient.

After calculating the correction coefficient, the correction coefficient determination unit 505 sends a corrosion amount calculation instruction signal to the corrosion amount calculation unit 506.

When the corrosion amount calculation unit 506 receives the corrosion amount calculation instruction signal from the correction coefficient determination unit 505, the corrosion amount calculation unit 506 calculates the corrosion amount of the measuring QCM sensor 10. The corrosion amount of the measuring QCM sensor 10 is calculated by using expression (1) based on the mass increase amounts of the measuring QCM sensor 10 and the reference QCM sensor 20, which are calculated by the mass increase amount determination unit 504, and the correction coefficient calculated by the correction coefficient determination unit 505.

When the alert output unit 507 receives the non-fitting signal and the non-fitting time zone signal from the frequency/humidity examination unit 503, the alert output unit 507 transmits a non-fitting alert signal and the non-fitting time zone signal to the interface unit 42. When the alert output unit 507 receives the fitting fail signal from the frequency/humidity examination unit 503, the alert output unit 507 transmits a fitting fail alert signal to the interface unit 42. When the alert output unit 507 receives the calculation number shortage signal from the mass increase amount determination unit 504, the alert output unit 507 transmits a calculation number shortage alert signal to the interface unit 42.

When the interface unit 42 receives the fitting fail alert signal and the non-fitting time zone signal, the interface unit 42 displays a fitting fail alert along with the time zone corresponding to the non-fitting time zone signal. When the interface unit 42 receives the fitting fail alert signal, the interface unit 42 displays the fitting fail alert. When the interface unit 42 receives the calculation number shortage alert signal, the interface unit 42 displays a calculation number shortage alert.

Figure 14:
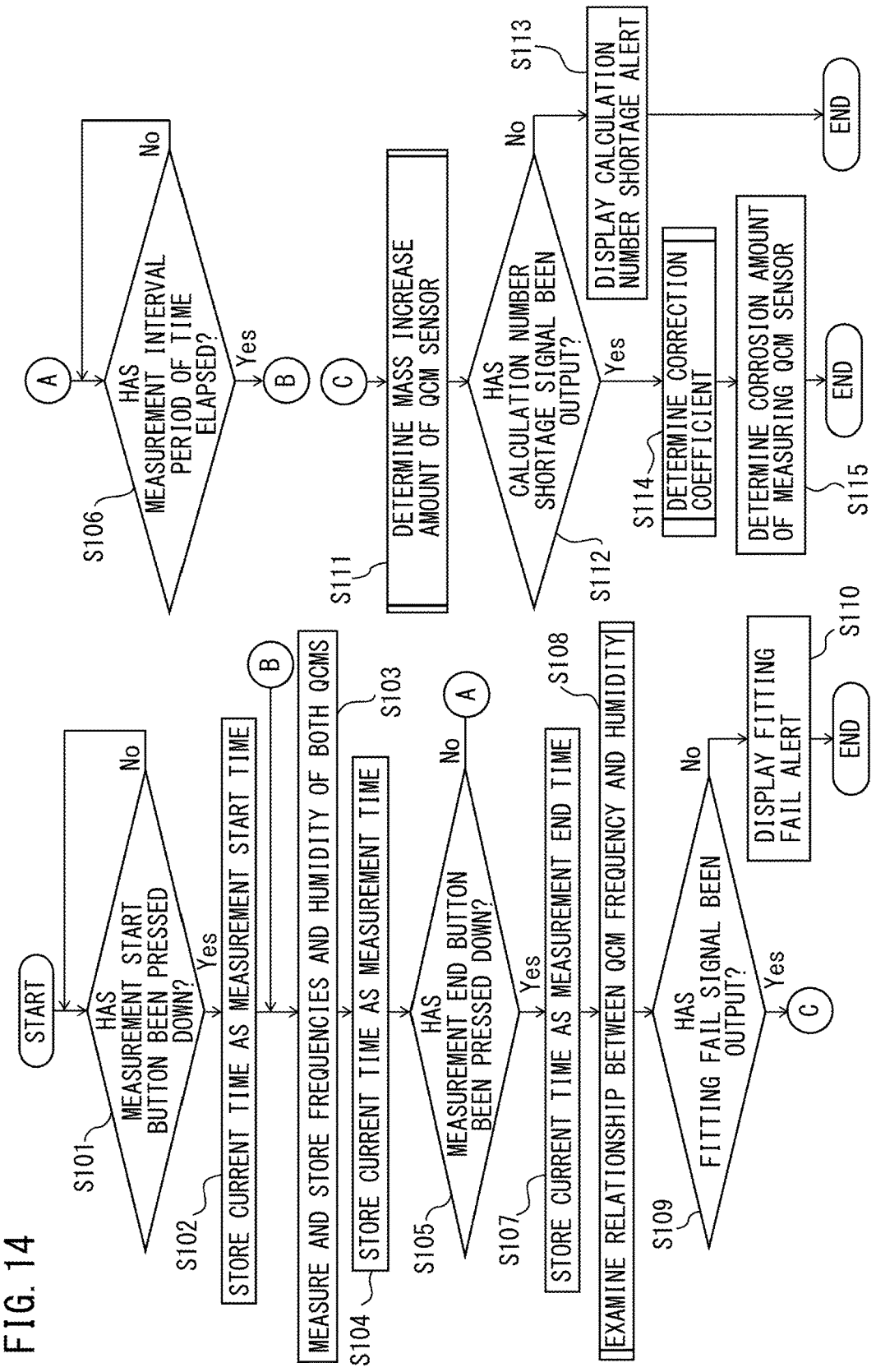
FIG. 14 is a flowchart illustrating control processing.

FIG. 14 is a flowchart illustrating control processing of the control unit 50.

First, at step S101, the device activation/deactivation unit 501 determines whether the measurement start button has been pressed down. Specifically, the device activation/deactivation unit 501 determines whether the measurement start command signal has been received from the interface unit 42. If the device activation/deactivation unit 501 determines that the measurement start command signal has not been received from the interface unit 42, the processing returns to step S101 again after a predetermined period of time elapses. If the device activation/deactivation unit 501 determines that the measurement start command signal has been received from the interface unit 42, the processing proceeds to step S102.

Next, at step S102, the device activation/deactivation unit 501 stores the current time in the storage unit 41 as a measurement start time.

Next, at step S103, the measurement unit 502 measures the frequencies of the measuring QCM sensor 10 and the reference QCM sensor 20 and humidity, and stores the measuring QCM counter signal, the reference QCM counter signal, and the humidity signal in the storage unit 41 after associating them with one another.

Next, at step S104, the measurement unit 502 stores the current time in the storage unit 41 as a measurement time signal. The measurement unit 502 stores the measurement time signal in the storage unit 41 after associating the measurement time signal with the measuring QCM counter signal, the reference QCM counter signal, and the humidity signal stored at step S103.

Next, at step S105, the device activation/deactivation unit 501 determines whether the measurement end button has been pressed down.

Specifically, the device activation/deactivation unit 501 determines whether the measurement end command signal has been received from the interface unit 42. If the device activation/deactivation unit 501 determines that the measurement end command signal has not been received from the interface unit 42, the processing proceeds to step S106. If the device activation/deactivation unit 501 determines that the measurement end command signal has been received from the interface unit 42, the processing proceeds to step S107.

When the processing proceeds to step S106, the measurement unit 502 determines whether the measurement interval period of time has elapsed by comparing the most recent time of the times stored in the storage unit 41 as the measurement times with the current time. If the measurement unit 502 determines that a QCM measurement interval time has not elapsed, the processing returns to step S106 again after the predetermined period of time elapses. If the measurement unit 502 determines that the QCM measurement interval time has elapsed, the processing returns to step S103.

The measurement unit 502 repeatedly performs the processing at steps S103 to S106 for each measurement interval period of time until the device activation/deactivation unit 501 determines that the measurement end command signal has been received from the interface unit 42 at step S105.

Since the measurement unit 502 repeatedly performing the processing at steps S103 to S106, the measuring QCM counter signal, the reference QCM counter signal, and the humidity signal each being associated with the measurement time are stored sequentially in the storage unit 41.

If it is determined that the measurement end button has been pressed down at step S106 and the processing proceeds to step S107, the device activation/deactivation unit 501 stores the current time in the storage unit 41 as a measurement end time.

Next, at step S108, the frequency/humidity examination unit 503 examines whether the relationship between each frequency and humidity is the relationship illustrated in FIG. 8 from the relationship between the frequencies of the measuring QCM sensor 10 and the reference QCM sensor 20 and the humidity, which are stored in the storage unit 41.

Next, at step S109, the device activation/deactivation unit 501 determines whether the fitting fail signal has been output. If the device activation/deactivation unit 501 determines that the fitting fail signal has not been output, the processing proceeds to step S111. On the other hand, if the device activation/deactivation unit 501 determines that the fitting fail signal has been output, the processing proceeds to step S110.

When the processing proceeds to step S110, the alert output unit 507 transmits the fitting fail alert signal to the interface unit 42, and the interface unit 42 displays the fitting fail alert.

When the processing proceeds to step S111, the mass increase amount determination unit 504 determines the mass increase amount due to the corrosion of the electrode of the measuring QCM sensor 10 and the particles having adhered to the measuring QCM sensor 10, and the mass increase amount due to the particles having adhered to the reference QCM sensor 20.

Next, at step S112, the device activation/deactivation unit 501 determines whether the calculation number shortage signal has been output. If the device activation/deactivation unit 501 determines that the calculation number shortage signal has not been output, the processing proceeds to step S113. On the other hand, if the device activation/deactivation unit 501 determines that the calculation number shortage signal has been output, the processing proceeds to step S114.

When the processing proceeds to step S113, the alert output unit 507 transmits the calculation number shortage alert signal to the interface unit 42, and the interface unit 42 displays the calculation number shortage alert.

When the processing proceeds to step S114, the correction coefficient determination unit 505 determines the correction coefficient.

Then, at step S115, the corrosion amount calculation unit 506 calculates the corrosion amount of the measuring QCM sensor 10 by using expression (1).

Figure 15:
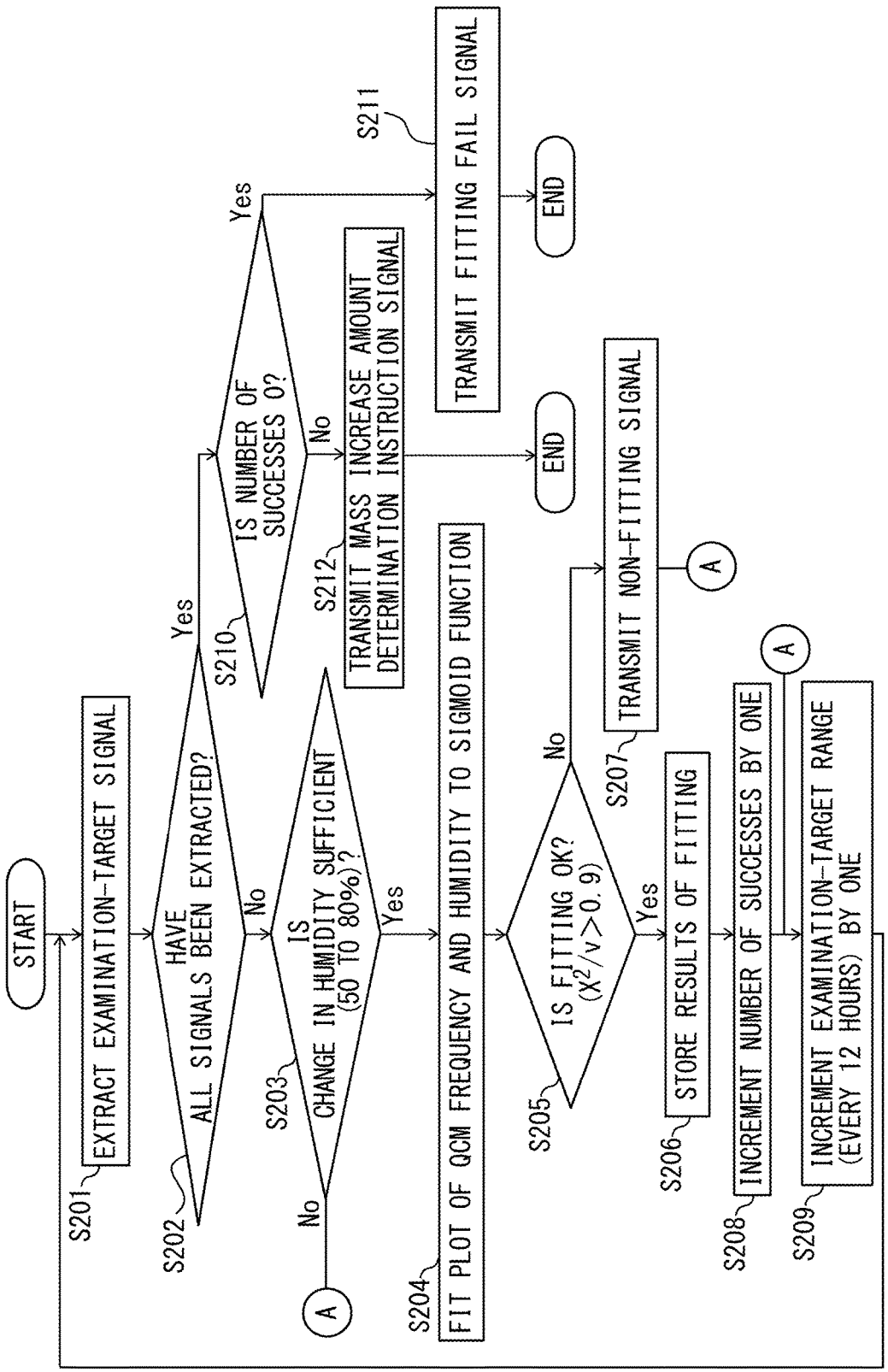
FIG. 15 is a flowchart of the processing flow of one processing illustrated in FIG. 14.

FIG. 15 is a flowchart of the processing flow of the frequency/humidity examination processing illustrated as step S108 in FIG. 14.

First, at step S201, the frequency/humidity examination unit 503 extracts the measuring QCM sensor frequency signal and the reference QCM sensor frequency signal, which are to be examined. The measuring QCM sensor frequency signal and the reference QCM sensor frequency signal, which are extracted, are signals whose measurement time is within 12 hours from the measurement start.

Next, at step S202, the frequency/humidity examination unit 503 determines whether all the measuring QCM sensor frequency signals and the reference QCM sensor frequency signals have been extracted. If the frequency/humidity examination unit 503 determines that all the measuring QCM sensor frequency signals and the reference QCM sensor frequency signals have been extracted, the processing proceeds to step S210. If the frequency/humidity examination unit 503 determines that all the measuring QCM sensor frequency signals and the reference QCM sensor frequency signals have not been extracted, the processing proceeds to step S203.

When the processing proceeds to step S203, the frequency/humidity examination unit 503 determines whether the change in the humidity corresponding to the humidity signal associated with the extracted measuring QCM sensor frequency signal and with the extracted reference QCM sensor frequency signal is sufficient. The frequency/humidity examination unit 503 determines whether the number of humidity signals whose humidity corresponding to the associated humidity signal is 50% to 80% is larger than a predetermined threshold number. If the frequency/humidity examination unit 503 determines that the change in humidity is not sufficient, the processing proceeds to step S209. If the frequency/humidity examination unit 503 determines that the change in humidity is sufficient, the processing proceeds to step S204.

When the processing proceeds to step S204, the frequency/humidity examination unit 503 fits the plot of the frequencies corresponding to the extracted measuring QCM sensor frequency signal and the extracted reference QCM sensor frequency signal and the humidity corresponding to the associated humidity signal to the sigmoid function.

Next, at step S205, the frequency/humidity examination unit 503 determines whether the plotted graph fits to the sigmoid function. If the plotted graph satisfies the relationship of ($X^2$/V>0.9), the frequency/humidity examination unit 503 determines that the plotted graph fits to the sigmoid function. If the frequency/humidity examination unit 503 determines that the plotted graph fits to the sigmoid function, the processing proceeds to step S206. If the frequency/humidity examination unit 503 determines that the plotted graph does not fit to the sigmoid function, the processing proceeds to step S207.

When the processing proceeds to step S206 in accordance with the determination at step S205, the frequency/humidity examination unit 503 stores the results of the fitting in the storage unit 41 and the processing proceeds to step S208.

Next, at step S208, the frequency/humidity examination unit 503 increments the number of successes and the processing proceeds to step S209.

When the processing proceeds to step S207 in accordance with the determination at step S205, the frequency/humidity examination unit 503 transmits the non-fitting signal and the non-fitting time zone signal indicating the time zone during which the fitting fails to the alert output unit 507, and the processing proceeds to step S209.

Next, at step S209, the frequency/humidity examination unit 503 increments the range to be examined (hereinafter, examination-target range). In other words, by incrementing the examination-target range, the frequency/humidity examination unit 503 moves the examination target to the next 12-hour examination-target range. Then, the processing returns to step S201.

The frequency/humidity examination unit 503 repeats the processing at steps S201 to S209 until determining that all the measuring QCM sensor frequency signals and the reference QCM sensor frequency signals have been extracted at step S202. If the frequency/humidity examination unit 503 determines that all of the measuring QCM sensor frequency signals and the reference QCM sensor frequency signals have been extracted at step S202, the processing proceeds to step S210.

When the processing proceeds to step S210, the frequency/humidity examination unit 503 determines whether the number of successes in which the fitting is determined to be successful is zero. If the frequency/humidity examination unit 503 determines that the number of successes in which the fitting is determined to be successful is zero, the processing proceeds to step S211. If the frequency/humidity examination unit 503 determines that the number of successes in which the fitting is determined to be successful is not zero, the processing proceeds to step S212.

When the processing proceeds to step S211, the frequency/humidity examination unit 503 transmits the fitting fail signal to the alert output unit 507. When the processing proceeds to step S212, the frequency/humidity examination unit 503 transmits the mass increase amount determination instruction signal to the mass increase amount determination unit 504.

Figure 16:
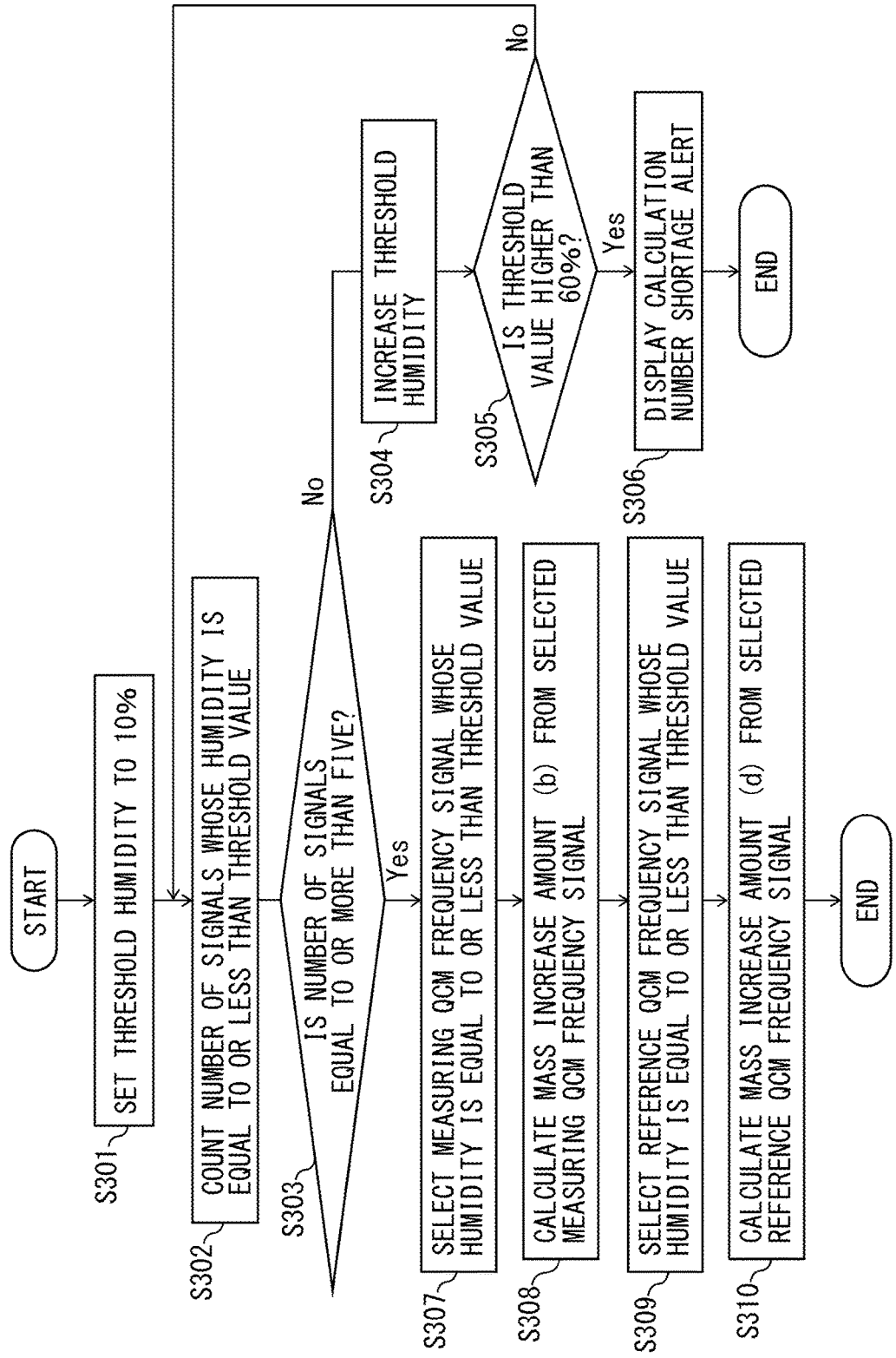
FIG. 16 is a flowchart of the processing flow of other processing illustrated in FIG. 14.

FIG. 16 is a flowchart of a processing flow of mass increase amount determination processing illustrated as step S111 in FIG. 14.

First, at step S301, the mass increase amount determination unit 504 sets the threshold humidity to 10%.

Next, at step S302, the mass increase amount determination unit 504 counts the number of humidity signals whose humidity corresponding to the humidity signal stored in the storage unit 41 is equal to or less than 10%.

Next, at step S303, the mass increase amount determination unit 504 determines whether the counted number of humidity signals is equal to or more than five. If the mass increase amount determination unit 504 determines that the counted number of humidity signals is not equal to or more than five, the processing proceeds to step S304. If the mass increase amount determination unit 504 determines that the counted number of humidity signals is equal to or more than five, the processing proceeds to step S307.

When the processing proceeds to step S304, the mass increase amount determination unit 504 sets the threshold humidity to 20% by increasing the threshold humidity by 10%.

Next, at step S305, the mass increase amount determination unit 504 determines whether the threshold humidity is higher than 60%. If the mass increase amount determination unit 504 determines that the threshold humidity is not higher than 60%, the processing returns to step S302. If the mass increase amount determination unit 504 determines that the threshold humidity is higher than 60%, the processing proceeds to step S306.

The mass increase amount determination unit 504 repeatedly performs the processing at steps S302 to S305 until determining that the counted number of humidity signals is equal to or more than five at step S303 or determining that the threshold humidity is higher than 60% at step S305.

When the processing proceeds to step S307, the mass increase amount determination unit 504 selects the measuring QCM counter signal that is associated with the humidity signal to be counted and which is selected.

Next, at step S308, the mass increase amount determination unit 504 calculates the mass increase amount due to the corrosion of the electrode of the measuring QCM sensor 10 and the particles having adhered to the measuring QCM sensor 10.

Next, at step S309, the mass increase amount determination unit 504 selects the reference QCM counter signal that is associated with the humidity signal to be counted and which is selected.

Next, at step S310, the mass increase amount determination unit 504 calculates the mass increase amount due to the particles having adhered to the reference QCM sensor 20.

When the processing proceeds to step S306, the mass increase amount determination unit 504 transmits the calculation number shortage signal to the alert output unit 507.

Figure 17:
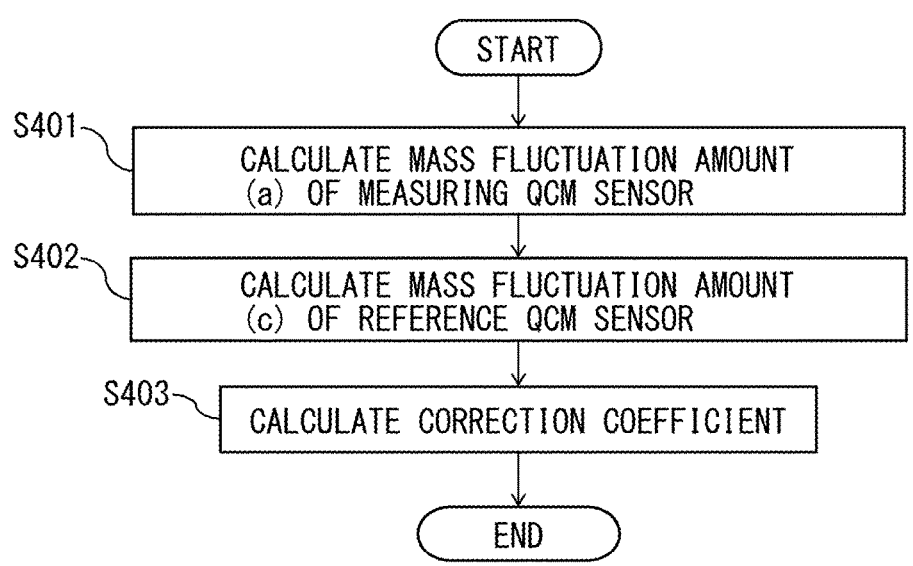
FIG. 17 is a flowchart of the processing flow of other processing illustrated in FIG. 14.

FIG. 17 is a flowchart of a processing flow of correction coefficient determination processing illustrated as step S114 in FIG. 14.

First, at step S401, the correction coefficient determination unit 505 calculates the mass fluctuation amount due to the moisture absorption—drying cycle of the particles having adhered to the measuring QCM sensor 10.

Next, at step S402, the correction coefficient determination unit 505 calculates the mass fluctuation amount due to the moisture absorption—drying cycle of the particles having adhered to the reference QCM sensor 20.

Then, at step S403, the mass increase amount determination unit 504 calculates the correction coefficient. The mass increase amount determination unit 504 calculates the slope of the first-order approximate straight line as the correction coefficient, which is obtained by plotting the calculated mass fluctuation amounts due to the moisture absorption—drying cycle of the particles having adhered to the measuring QCM sensor 10 and the reference QCM sensor 20 by associating the mass fluctuation amounts with humidity.

In the environment measuring device 1, the corrosion amount of the measurement electrode 12 of the measuring QCM sensor 10 is determined by using the measurement count signal and the reference count signal each indicating the frequency measured at humidity equal to or less than predetermined humidity. Because the measurement count signal and the reference count signal each indicating the frequency measured at humidity equal to or less than predetermined humidity are used, the influence of the mass fluctuations due to the moisture absorption—drying cycle of the particles having adhered to the measuring QCM sensor 10 and the reference QCM sensor 20 is eliminated.

In the environment measuring device 1, the corrosion amount of the measurement electrode 12 of the measuring QCM sensor 10 is determined by using the correction coefficient for correcting the difference in number between the particles having adhered to the measuring QCM sensor 10 and the particles having adhered to the reference QCM sensor 20. In the environment measuring device 1, since the corrosion amount is determined by using the correction coefficient for correcting the difference in number between the particles having adhered to both sensors, the corrosion amount with a high degree of accuracy may be determined, even if the number of particles having adhered to the measuring QCM sensor 10 is different from the number of particles having adhered to the reference QCM sensor 20.

In the environment measuring device 1, the correction coefficient is calculated from the ratio between the magnitude of the mass fluctuation amount due to the moisture absorption—drying cycle of the particles having adhered to the measuring QCM sensor 10 and the magnitude of the mass fluctuation amount due to the moisture absorption—drying cycle of the particles having adhered to the reference QCM sensor 20. In the environment measuring device 1, the correction coefficient that is calculated from the ratio between the magnitudes of the mass fluctuation amounts due to the moisture absorption—drying cycle of the particles having adhered to both sensors, and therefore the correction in which the number of particles having adhered is reflected is enabled.

In the environment measuring device 1, the measurement electrode 12 of the measuring QCM sensor 10 is formed by silver, however may be formed by another corrosive metal or alloy. Further, the reference electrode 22 of the reference QCM sensor 20 is formed by gold, however may be formed by another corrosion-resistant metal or alloy.

In the environment measuring device 1, the mass increase amount determination unit 504 calculates the approximate straight line based on the five frequency signals, however the number of frequency signals used to calculate the approximate straight line may be smaller than five or larger than five. Further, although the mass increase amount determination unit 504 increases the threshold humidity by 10% each time in order to calculate the approximate straight line, the threshold humidity may be increased by an appropriate amount each time, such as 5%.

In the environment measuring device 1, the correction coefficient is calculated from the ratio between the magnitudes of the mass fluctuation amounts due to the moisture absorption—drying cycle of the particles having adhered to the measuring QCM sensor 10 and the reference QCM sensor 20, respectively. However, if the ratio between the mass of the particles having adhered to the measuring QCM sensor 10 and the mass of the particles having adhered to the reference QCM sensor 20 is already known, the correction coefficient may be calculated from the already-known ratio of mass. In the environment in which the mass of the particles that adhere to the measuring QCM sensor 10 is the same as the mass of the particles that adhere to the reference QCM sensor 20, the mass increase amount due to the corrosion of the electrode of the measuring QCM sensor 10 may be determined without using the correction coefficient.

All examples and conditional language provided herein are intended for pedagogical purposes of aiding the reader in understanding the invention and the concepts contributed by the inventor to furthering the art, and are to be construed as limitations to such specifically recited examples and conditions, nor does the organization of such examples in the specification relate to a illustrating of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An environment measuring device comprising:
   a measuring QCM sensor having an oscillator and an electrode formed of a corrosive metal on a surface of the oscillator;
   a reference QCM sensor having an oscillator and an electrode formed of a corrosion-resistant metal on a surface of the oscillator;
   a measurement oscillation circuit configured to transmit a measurement frequency signal having a frequency in accordance with a number of oscillations of the measuring QCM sensor as well as oscillating the measuring QCM sensor;
   a reference oscillation circuit configured to transmit a reference frequency signal having a frequency in accordance with a number of oscillations of the reference QCM sensor as well as oscillating the reference QCM sensor;
   a frequency counter that is connected to the measurement oscillation circuit and the reference oscillation circuit, counts a frequency of each of the measurement frequency signal and the reference frequency signal, and transmits a measurement count signal and a reference count signal each indicating a counted number;

a humidity sensor configured to detect humidity in an atmosphere and to transmit a humidity signal indicating the detected humidity;

a storage unit configured to store the measurement count signal, the reference count signal, and the humidity signal which are associated with a measurement time; and a control unit configured to determine a mass increase amount due to corrosion of the electrode of the measuring QCM sensor by using an approximate expression calculated from measurement count signals and reference count signals indicating frequencies measured at humidity equal to or less than 60% and measurement time.

2. The environment measuring device according to claim 1, wherein the control unit uses a correction coefficient for correcting a difference in number between particles having adhered to the measuring QCM sensor and particles having adhered to the reference QCM sensor when determining a mass increase amount due to the corrosion of the electrode of the measuring QCM sensor.

3. The environment measuring device according to claim 2, wherein the correction coefficient is calculated from a ratio between magnitude of a mass fluctuation amount due to a moisture absorption—drying cycle of the particles having adhered to the measuring QCM sensor and the magnitude of a mass fluctuation amount due to the moisture absorption—drying cycle of the particles having adhered to the reference QCM sensor.

4. An environment measuring method comprising:

measuring a frequency of a measuring QCM sensor having an oscillator and an electrode formed by a corrosive metal on a surface of the oscillator when the measuring QCM sensor resonates with a measurement oscillation circuit;

calculating mass increase amounts of the measuring QCM sensor from a frequency of the measuring QCM sensor at humidity equal to or less than 60%;

measuring a frequency of a reference QCM sensor having an oscillator and an electrode formed by a corrosion-resistant metal on a surface of the oscillator when the reference QCM sensor resonates with a reference oscillation circuit;

calculating mass increase amounts of the reference QCM sensor from a frequency of the reference QCM sensor at humidity equal to or less than the 60%; and determining a mass increase amount due to corrosion of the electrode of the measuring QCM sensor by using an approximate expression calculated from the mass increase amounts of the measuring QCM sensor, the mass increase amounts of the reference QCM sensor and measuring time.

5. The environment measuring method according to claim 4, wherein when determining the mass increase amount due to the corrosion of the electrode of the measuring QCM sensor, a correction coefficient for correcting a difference in number between particles having adhered to the measuring QCM sensor and particles having adhered to the reference QCM sensor is used.

6. The environment measuring method according to claim 5, wherein the correction coefficient is calculated from a ratio between a magnitude of a mass fluctuation amount due to a moisture absorption—drying cycle of the particles having adhered to the measuring QCM sensor and a magnitude of a mass fluctuation amount due to the moisture absorption—drying cycle of the particles having adhered to the reference QCM sensor.

\* \* \* \* \*